United States Patent [19]
Barker, Jr. et al.

[11] Patent Number: 4,573,010
[45] Date of Patent: Feb. 25, 1986

[54] MINIATURE CELL ADAPTOR TO ACCOMMODATE SMALL SAMPLES IN RESISTIVITY CELLS

[75] Inventors: Robert E. Barker, Jr., Charlottesville, Va.; Daniel Y. Chen, Pullman, Wash.

[73] Assignee: The United States of America as represented by the Secretary of the Air Force, Washington, D.C.

[21] Appl. No.: 528,309

[22] Filed: Aug. 31, 1983

[51] Int. Cl.$^4$ .................... G01R 31/02; G01R 27/02; H01C 1/022
[52] U.S. Cl. .................... 324/158 F; 324/62; 324/65 P; 324/158 P; 338/232; 338/328
[58] Field of Search .............. 324/158 F, 158 P, 65 P, 324/61 P, 62; 338/232, 233, 254, 256, 318, 328

[56] References Cited
U.S. PATENT DOCUMENTS

| | | | |
|---|---|---|---|
| 581,170 | 4/1897 | Nebel | 338/233 |
| 2,806,930 | 9/1957 | Yager | 324/62 |
| 2,982,912 | 5/1961 | Mitchell, Jr. | 324/65 P |
| 2,993,368 | 7/1961 | Schlein | 73/807 |
| 3,458,807 | 7/1969 | Smith | 324/73 R |
| 3,912,983 | 10/1975 | Lowry, Jr. | 324/158 F |
| 4,340,860 | 7/1982 | Teeple, Jr. | 324/158 F |

Primary Examiner—Ernest F. Karlsen
Attorney, Agent, or Firm—Donald J. Singer; Bobby D. Scearce

[57] ABSTRACT

An adaptor for supporting small thin film or fibrous samples of material between the electrodes of a resistivity cell is described which comprises a pair of stacked electrically insulating plates, each plate having a central electrode therethrough and presenting confronting conductive surfaces of known surface area for sandwiching the sample therebetween for resistivity measurement, and a guarding electrode on one confronting plate surface and surrounding the central electrode thereon for electrically contacting the guarding electrode of the resistivity cell; the plates may be hingedly joined along respective sides and include fittings to maintain the confronting electrode surfaces in concentric alignment with the sample therebetween.

5 Claims, 5 Drawing Figures

MINIATURE CELL ADAPTOR TO ACCOMMODATE SMALL SAMPLES IN RESISTIVITY CELLS

RIGHTS OF THE GOVERNMENT

The invention described herein may be manufactured and used by or for the Government of the United States for all governmental purposes without the payment of any royalty.

BACKGROUND OF THE INVENTION

This invention relates generally to devices for the measurement of electrical properties of materials, and more particularly to a novel miniaturized test cell for making resistivity measurements and the like on materials in very small sample sizes.

In the measurement of the electrical properties of materials, such as the conductivity, resistivity, dielectric constants, etc., measuring techniques and instrumentation have been well documented in the art.

The use of commercially available electrometers or resistivity cells, however, require that a certain minimum sample quantity is available to prepare samples in appropriate sizes for examination. For example, commercially available resistivity cells ordinarily require a minimum sample size of about ten centimeters in diameter and seven millimeters in thickness, and, further, that the sample exhibit a certain minimum degree of dimensional stability under moderate compression. Use of these measurement instruments is very impractical for small, research size samples, such as fine fibers or thin films. The ability to make desirable measurements on very small samples is therefore limited, which, in turn, limits the capability to make certain measurements on newly developed materials which may be in extremely short supply. Further, the use of new or existing materials in advanced technology applications wherein the materials are configured for use in the form of thin films or fine fibers may require electrical property measurements to characterize these materials as thin films or fibers, which is not feasible in existing instrumentation.

The present invention solves or reduces in critical importance the foregoing problems with existing instrumentation by providing an improved miniaturized test cell for measuring certain electrical properties of samples of very small size. Specifically, the invention comprises a pair of insulated plates appropriately fitted with precisely prepared electrodes for sandwiching a sample therebetween, the assembly being configured to be inserted between the electrodes of a conventional resistivity cell. The invention allows the examination of samples comprising fine (less than about 20 microns diameter) fibers or small (about 6 mm square×20 microns thick) thin film specimens, although both thinner and thicker samples could be used.

It is, therefore, a principal object of the present invention to provide an adaptor for accommodating very small sample sizes in resistivity cells.

It is a further object of the invention to provide a miniaturized resistivity cell for use in conjunction with existing instrumentation for electrical property measurement of very small samples.

These and other objects of the present invention will become apparent upon further reading of the detailed description of certain representative embodiments thereof.

SUMMARY OF THE INVENTION

In accordance with the foregoing principles and objects of the present invention, an adaptor for supporting small thin film or fibrous samples of material between the electrodes of a resistivity cell is described which comprises a pair of stacked electrically insulating plates, each plate having a central electrode therethrough and presenting confronting conductive surfaces of known surface area for sandwiching the sample therebetween for resistivity measurement, and a guarding electrode on one confronting plate surface and surrounding the central electrode thereon for electrically contacting the guarding electrode of the resistivity cell; the plates may be hingedly joined along respective sides and include fittings to maintain the confronting electrode surfaces in concentric alignment with the sample therebetween.

DESCRIPTION OF THE DRAWINGS

The present invention will be more clearly understood from the following detailed description of certain representative embodiments thereof read in conjunction with the accompanying drawings wherein.

DETAILED DESCRIPTION

Figure 1:
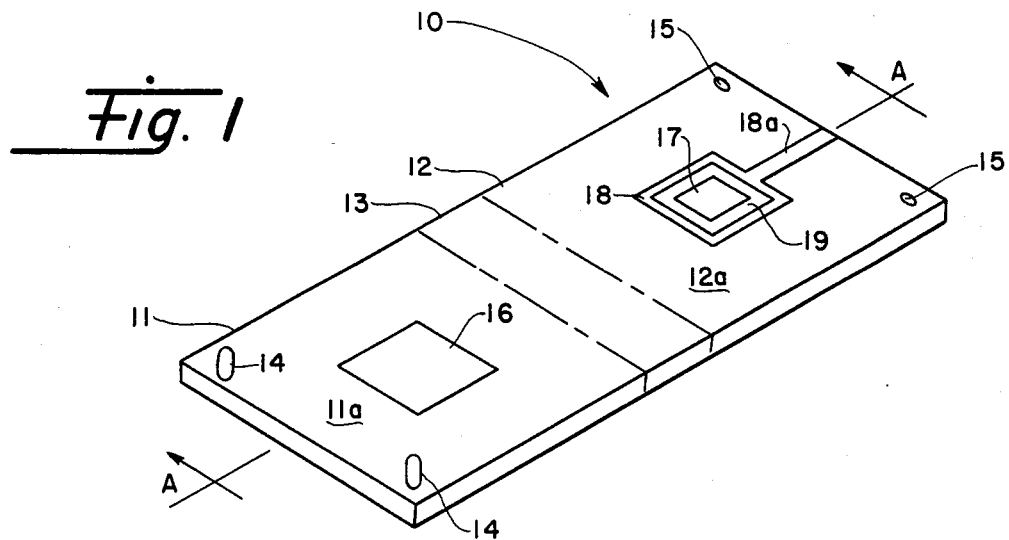
FIG. 1 is an isometric view of the miniaturized adaptor of the present invention.

Referring now to FIG. 1 of the drawings, shown therein is an isometric view of one embodiment of the miniature guarded electrode adaptor of the present invention. The adaptor 10 as depicted in FIG. 1 represents the embodiment of the present invention particularly suited for accommodating thin, ribbon-like samples.

Adaptor 10 comprises a pair of thin plates 11 and 12 of electrically insulating material for supporting the electrodes of the miniature guarded electrode system of the present invention. In the assembled condition, as hereinafter described, plates 11 and 12 are intended to sandwich a sample between confronting faces 11a and 12a. For the purpose of clarity in describing the structure of adaptor 10, FIG. 1 shows adaptor 10 in the open or unfolded configuration exposing the (inner) surfaces of plates 11, 12 between which the sample is inserted.

Plates 11, 12 may comprise thin (about 2 mm) sheets of any suitable electrically insulating material exhibiting suitable structural properties for adequately supporting the electrodes. Adaptors 10 constructed in demonstration of the invnetion herein comprises Lexan ® polycarbonate or Mylar ® polyethylene terephthalate sheets. It is understood, however, that these materials of construction for plates 11, 12 shall not be limiting of the invention herein, as other suitable insulating materials may be used as would occur to one with skill in the applicable field. In order to conveniently sandwich a sample between the confronting inner surfaces 11a, 12a, plates 11, 12 may be hingedly joined in any convenient fashion along respective adjacent sides such as suggested in FIG. 1 as hinge 13. In the embodiment depicted in FIG. 1, hinge 13 comprises a flexible portion of the structural material comprising plates 11 and 12, so that plates 11 and 12 and hinge 13 could be formed as one integral foldable piece. It is understood, however, that plates 11 and 12 could be otherwise hingedly joined. Further, and within the intended scope of the present invention plates 11, 12 may comprise separate plates having suitable alignment and/or clamping means to ensure proper alignment of the electrodes with a sample. For either of the described plate 11, 12 configurations, snap fittings or other alignment means, such as shown in FIG. 1 as alignment pegs 14 and mating alignment holes 15 may be included to ensure reproducible, precise alignment of surface 11a with surface 12a in the assembled condition.

Figure 1A:
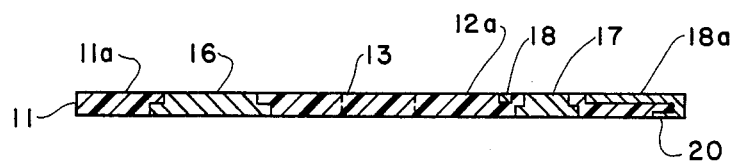
FIG. 1a is a cross-sectional view of the adaptor of FIG. 1 as viewed along lines A—A thereof.

Plate 11, hereinafter referred to as upper plate 11, includes a centrally located upper electrode 16 having any desirable peripheral shape and comprising copper or other highly conductive metal. Referring additionally to FIG. 1a, which is a sectional view of adaptor 10 taken along lines A—A of FIG. 1, electrode 16 may preferably have a substantially square configuration molded or otherwise firmly held within plate 11 and presenting conductive surfaces in both the inner (11a) and outer surfaces of plate 11. The overall shape of electrode 16, and of the other electrodes hereafter described, may vary depending on sample shape, type of resistivity cell used, etc., and will ordinarily have an inner surface area consistent with the size of the sample. Electrode 16 is configured to provide electrical contact between the upper electrode of a resistivity cell (contacting electrode 16 at the outer surface of plate 11) and a sample 21 (see FIG. 2) in contact with electrode 16 at the inner surface 11a of plate 11. The surface area of electrode 16 contacting sample 21 will, of course, be of known, predetermined size, for example, substantially the same as the size of sample 21 or ideally, somewhat smaller than sample 21.

Plate 12 (also lower plate 12) has a guarded, centrally located mini-electrode 17, of copper or other conducting metal, presenting conductive surfaces to both the inner (12a) and outer surfaces of plate 12 substantially as shown in FIG. 1a. The electrode 17 may be of any desirable shape although it will generally be of the same shape as, though smaller in surface area than, electrode 16. Electrode 17 is located substantially central of plate 12 such that it will confront electrode 16 with a known, predetermined confronting surface area when plate 11 is folded onto plate 12 in the assembly of adaptor 10. Electrode 17 is configured to provide electrical contact between the sample 21 (see FIG. 2) at the inner surface 12a of plate 12 and the central guarded electrode of the resitivity cell (reference number 23 of FIG. 2).

Surrounding electrode 17 and applied to the upper surface 12a of plate 12 is a marginal guarding electrode 18 having the same general shape as, though larger than, electrode 17 and sized and placed to confront electrode 16 concentrically when adaptor 10 is assembled. Electrode 18 is electrically insulated from electrode 17 by a marginal region 19 of surface 12a. Conducting strip 18a electrically connects electrode 18 with an electrical contact 20 on the outer side of plate 12 substantially as shown in FIG. 1a. Guarding electrode 18, conducting strip 18a and contact 20 provide electrical connection with the guarding electrode of the resistivity cell as suggested in FIG. 2. Guarding electrode 18 serves to eliminate surface leakage effects in adaptor 10 in manner consistent with the operation of conventional resistivity cells. In operation, therefore, guarding electrode 18 and guarded electrode 17 are ordinarily held at substantially equal potentials to minimize any current flow between them.

In representative models of adaptor 10 fabricated in demonstration of the invention herein, the overall sizes of electrodes 16, 17 and 18 were selected to accommodate the sample 21 size, and the overall size of adaptor 10 and placement of electrical contact 20 was selected to be compatible with the resistivity cell within which adaptor 10 was intended for use. In the representative devices built, film samples 6 mm square and 10 microns thick were intended for test. Accordingly, guarded mini-electrode 17 was selected to be 3 mm square. The width of marginal region 19 between guarded electrode 17 and guarding electrode 18 was about 1 mm, although minimizing this width (e.g., to less than about 0.2 mm) may be preferred. As an illustration of the useably small overall size of adaptor 10, the size of plates 11, 12 in one representative device was such to allow approximately 38 mm from the center of electrode 17 to the edge of plate 12 at conducting strip 18a in order to accommodate the specific commercial cell in which the demonstration adaptor 10 was used.

It is understood that adaptor 10 may be fabricated using a wide range of techniques within the intended scope hereof, including, but not necessarily limited to molding, vapor deposition, machining, photolithographic processes, or a combination thereof.

Figure 2:
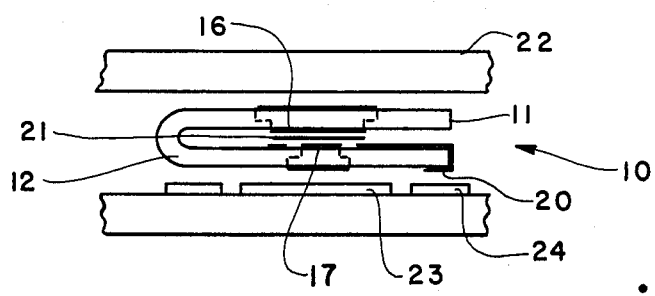
FIG. 2 is a side elevational view of the adaptor of the present invention in place between the electrodes of a conventional resistivity cell.

Referring now to FIG. 2, a thin film sample 21 may be tested substantially as follows. Sample 21 (about 6 mm by 6 mm) is inserted between confronting surfaces of electrodes 16 and 17 substantially as shown with plate 11 folded atop plate 12. Adaptor 10 is then inserted between the confronting surfaces of upper electrode 22 and lower electrodes 23 and 24 of the conventional resistivity cell. Upper electrode 22 of the conventional cell makes electrical contact with the outer (upper) surface of electrode 16 and electrode 17 makes contact at its outer (lower) surface with the guarded lower electrode 23 of the conventional cell; electrical contact 20 of adaptor 10 makes electrical contact with the guarding electrode 24 of the conventional cell.

Figure 3:
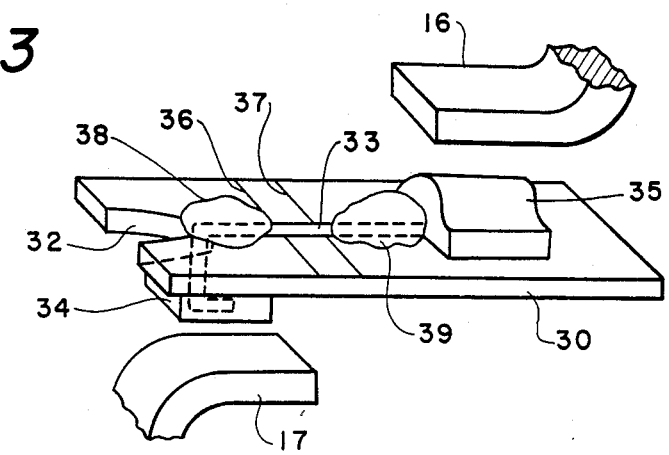
FIG. 3 presents an isometric view of a sample holder for testing fiber samples within the adaptor of the present invention.

The adaptor 10 of the present invention may be conveniently used in conjunction with a conventional resistivity cell for electrical measurements on samples comprising fine (less than about 100 microns) fibers, by suitable mounting of the sample on a sample base for insertion in adaptor 10. The mounted sample is then examined in manner similar to that described for sample 21 and as suggested in FIG. 2. Reference is now made to FIG. 3, which illustrates, on substantially enlarged scale, an example of the mounting configuration for a fibrous sample 33 and related electrodes for flowing electrical current through the sample using adaptor 10.

A small insulating base 30 having a notch 32 in one end thereof is provided for mounting of the fiber sample 33. Insulating base 30 may comprise any of the insulating materials suggested previously for plates 11, 12 of adaptor 10. For sample preparations made in successful demonstration of the invention herein, however, base 30 comprised Mylar ® sheet 70 microns thick and cut approximately 10 mm×15 mm. Notch 32 provided a convenient means to retain sample 33 centered on base 30. One end of sample 33 which had a total length of about 10 mm could then be secured at the underside of base 30 near notch 32 using a piece of electrically conducting copper tape 34. The other end of sample 33 was held at the upper surface of base 30 using a second piece of copper tape 35. A pair of parallel lines 36, 37 scribed on the surface of base 30 provided a gauging means to define a known effective length of the conducting pathway through fiber sample 33. For the demonstration devices, the spacing of lines 36, 37 was selected at 100 microns. Silver conducting paste was applied at 38, 39 adjacent, respectively, lines 36, 37 near each end of sample 33 to ensure good electrical contact with copper tape pieces 24, 35 and electrodes 17, 16, respectively, and to define the effective conducting path length through sample 33 (i.e., between silver paste connections 38, 39). The base 30 sample assembly could then be inserted into adaptor 10 between electrodes 16, 17 as suggested in FIG. 3.

Figure 4:
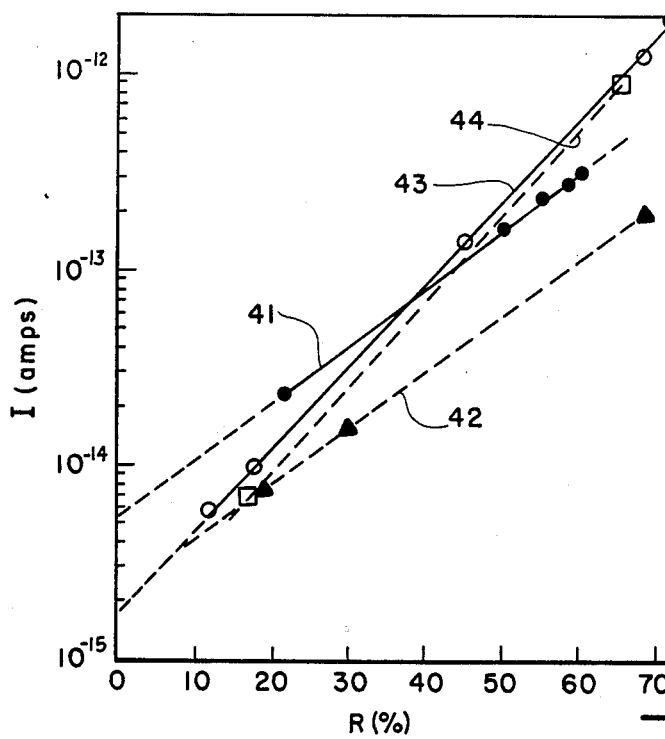
FIG. 4 presents data taken on representative film and fiber samples of a material tested in demonstration of the present invention.

The utility of the present invention was demonstrated through representative measurements taken on thin film and fine fiber samples of polyparaphenylene benzobisthiazole. FIG. 4 presents plots of current I (amps) vs relative humidity R (%) for both film and fiber samples. Plot 41 gives the data on measurements for a fiber 10 mm long by 20 microns in diameter; plot 42 is for a 10 mm long by 20 microns diameter fiber. Plots 43 and 44 are for 6 mm×6 mm film samples 30 microns thick and 20 microns thick, respectively. The linearity of the plots are an indication of the consistency of results obtainable using the adaptor of the present invention.

The preesnt invention, as hereinabove described, therefore provides a novel adaptor for facilitating electrical property measurements of samples of small size comprising thin films or fibers. It is understood that certain modifications to the invention as described may be made, as might occur to one with skill in the field of this invention, within the scope of the appended claims. Therefore, all embodiments contemplated hereunder have not been shown in complete detail. Other embodiments may be developed without departing from the spirit of this invention or from the scope of the appended claims.

We claim:

1. An adaptor for supporting small samples of material within a resistivity cell having first and second confronting electrodes and a guarding electrode for the second electrode comprising:
   a. a first electrically insulating plate having upper and lower surfaces and supporting a first central electrode therethrough, said first central electrode presenting a conductive surface at said upper first plate surface for contacting said first electrode of said resistivity cell, and presenting a second conductive surface of first predetermined size at said lower first plate surface for contacting said sample;
   b. a second electrically insulating plate having upper and lower surfaces and supporting a second central electrode therethrough, said second central electrode presenting a first conductive surface of second predetermined size smaller than said first predetermined size of said first central electrode at said upper second plate surface for contacting said sample, and a second conductive surface at said lower second plate surface for contacting said second electrode of said resistivity cell;
   c. a guarding electrode in the form of a first marginal conducting strip on said upper surface of said second plate, surrounding and electrically insulated from said second central electrode, and a second conducting strip for electrically interconnecting said marginal strip and said guarding electrode of said resistivity cell; and
   d. said first plate and said second plate disposed in confronting relationship for sandwiching said sample between confronting surfaces of said first and second central electrodes.

2. The adaptor as recited in claim 1 further comprising hinge means pivotally joining said first and second insulating plates along respective adjacent sides thereof.

3. The adaptor as recited in claim 1 further comprising alignment means on said first and second insulating plates for maintaining said lower surface of said first plate in confronting relationship with said upper surface of said second plate with said first and second central electrodes in substantialy concentric confronting registration with said sample therebetween.

4. The adaptor as recited in claim 1 further comprising a thin insulating plate for supporting a fiber sample of predetermined length within said adaptor and having a first electrical contact for interconnecting a first end of said fiber sample and said first central electrode, and a second electrical contact for interconnecting a second end of said fiber and said second central electrode, said thin insulating plate including means for gauging the length of said fiber sample between said first and second electrical contacts.

5. The adaptor as recited in claim 4 wherein said gauging means comprises a set of scored lines on said thin insulating plate, said lines having predetermined spacing with said first and second electrical contacts disposed, respectively, therebeside to define said predetermined length between said contacts.

* * * * *